United States Patent [19]

Wade et al.

[11] 3,995,045

[45] Nov. 30, 1976

[54] 2'-[(3,6-DIHYDRO-PHENYL-1(2H)PYRIDINYL)ALKYLAMINOCARBONYL][1,1'-BIPHENYL]-2-CARBOXYLIC ACIDS

[75] Inventors: Peter C. Wade, Pennington, N.J.; B. Richard Vogt, Yardley, Pa.

[73] Assignee: E. R. Squibb & Sons, Inc., Princeton, N.J.

[22] Filed: Sept. 25, 1975

[21] Appl. No.: 616,735

[52] U.S. Cl. .......................... 424/263; 260/293.77; 260/294.9; 260/295 AM; 424/267
[51] Int. Cl.² ........................................ C07D 213/56
[58] Field of Search ............... 260/294.9, 295 AM; 424/263

[56] References Cited
UNITED STATES PATENTS

| | | | |
|---|---|---|---|
| 2,929,818 | 3/1960 | Janssen | 260/295 AM |
| 3,927,006 | 12/1975 | Edenhofer | 260/295 A |

*Primary Examiner*—Alan L. Rotman
*Attorney, Agent, or Firm*—Lawrence S. Levinson; Merle J. Smith; Burton Rodney

[57] ABSTRACT

Compounds which are useful as anti-inflammatory agents have the formula

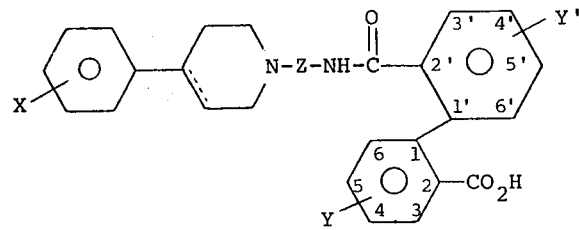

wherein X, Y, Y' and Z are as defined herein.

7 Claims, No Drawings

2'-[(3,6-DIHYDRO-PHENYL-1(2H)PYRIDINYL-)ALKYLAMINOCARBONYL][1,1'-BIPHENYL]-2-CARBOXYLIC ACIDS

This invention relates to 2'-[(3,6-dihydro-4-phenyl-1(2H)-pyridinyl or phenyl-1-piperidinyl)alkylamino carbonyl][1,1'-biphenyl]-2-carboxylic acids, and their acid or base addition salts, of the formula

I

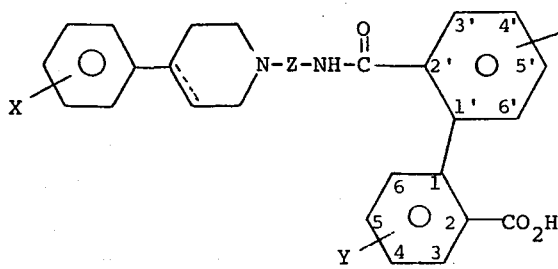

II

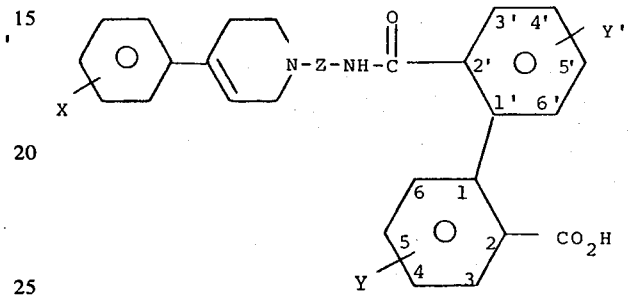

III or

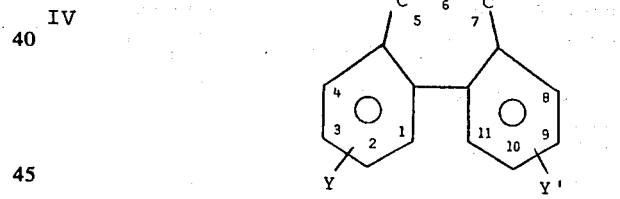

wherein X is hydrogen, lower alkyl, lower alkoxy, halogen, trifluoromethyl, amino or nitro; Y and Y' are the same and are hydrogen, halogen, trifluoromethyl, lower alkyl, lower alkoxy, nitro, amino or cyano, with the proviso that Y is at the 4- or 5-position and Y' is at the 4'- or 5'-position; provided that when Y is at the 4-position, Y' is at the 4'-position and when Y is at the 5-position, Y' is at the 5'-position; Z is a straight or branched chain alkylene group containing from 2 to 6 carbons; and the broken line (-----) represents an optional double bond.

The term "lower alkyl" as employed herein includes straight or branched chain aliphatic hydrocarbon radicals having up to four carbon atoms, such as methyl, ethyl, propyl, isopropyl, butyl, isobutyl, or t-butyl, and the like.

The term "lower alkoxy" as employed herein includes straight and branched chain radicals of the formula lower alkyl-O- wherein lower alkyl is as defined above, such as methoxy, ethoxy, propoxy, isopropoxy, and the like.

The term "halogen" includes F, Cl, Br, or I, but F, Br and Cl are preferred.

The alkylene radical Z includes straight or branched chain alkylene groups of 2 to 6 carbons, such as
—CH$_2$CH$_2$—,

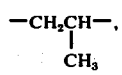

—CH$_2$CH$_2$CH$_2$CH$_2$—,

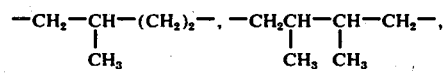

and the like.

Thus, it will be appreciated that the compounds of the present invention may have the following formulae:

Preferred are those compounds of formulae II and III wherein X is hydrogen, lower alkyl or halogen, Y and Y' are hydrogen, lower alkoxy or halogen, and Z is an alkylene group containing 2 to 4 carbons.

Most preferred are those compounds of formulae II and III wherein X, Y and Y' are each hydrogen and Z is an alkylene group containing 2 to 4 carbons.

The compounds of formula I of the invention are prepared as follows.

A diphenic anhydride of the formula IV

IV

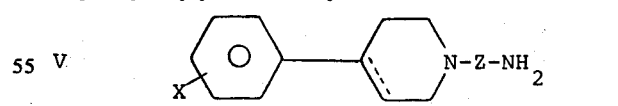

wherein Y and Y' are the same and Y is at the 2- or 3-position and Y' is at the 9- or 10-position; provided that when Y is at the 2-position, Y' is at the 10-position and when Y is at the 3-position, Y' is at the 9-position, is reacted with a (3,6-dihydro-4-phenyl-1(2H)pyridine or phenyl-1-piperidine)alkylamine of the formula

V

in the presence of a non-reacting solvent, such as toluene, 1,2-dimethoxyethane, dimethylformamide, benzene, xylene, or the like, employing an approximately 1:1 molar ratio of IV:V. The above reaction is carried out at temperatures ranging from about 0° to about 200° C, and preferably from about 50° to about 120° C, for from about 5 minutes to about 48 hours, and preferably from about 30 minutes to about 3 hours.

Where X, and/or Y and Y' are amino, they may optionally be produced at the last stage by reducing the corresponding nitro compounds using known techniques.

The diphenic anhydride starting materials (IV) are known in the art and may be prepared by cyclizing the corresponding diphenic acid with acetic anhydride as described in CA 52, 1964f(1957); CA 54, 8058b (1959).

The (3,6-dihydro-4-phenyl-1(2H)pyridine)alkylamine starting material of the formula Va are known in the art

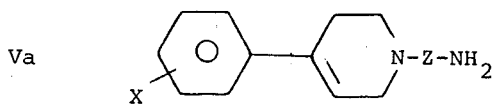

and may be prepared by alkylating a phenyl tetrahydropyridine with a halo alkyl nitrile and reducing the resulting nitrile with an appropriate reducing agent such as lithium aluminum hydride.

The (phenyl-1-piperidine)alkylamine starting material of formula Vb

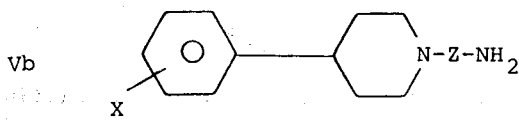

may be prepared as described above with respect to Va except that a phenylpiperidine is employed in place of the phenyl tetrahydropyridine.

The compounds of formula I form physiologically acceptable acid-addition salts or base addition salts with inorganic and organic acids or alkali metal or alkaline earth metal bases such as sodium hydroxide or calcium hydroxide. These salts frequently provide useful means for isolating the products from reaction mixtures by forming the salt in a medium in which it is insoluble. The free base may then be obtained by neutralization, e.g., with a base or acid. Then any other salt may again be formed from the free base and the appropriate inorganic acid or base. Illustrative are the hydrohalides, especially the hydrochloride and hydrobromide which are preferred, sulfate, nitrate, phosphate, oxalate, tartrate, maleate, fumarate, citrate, succinate, methanesulfonate, benzenesulfonate, toluenesulfonate, and the like.

The compounds of the invention are useful as anti-inflammatory agents as determined by the reverse passive arthus test [Agents & Actons, 5, 39 (1975)] and are effective in the prevention and inhibition of granuloma formation in warm blooded animals, and may be used, for example, in a manner similar to phenylbutazone or indomethacin. They may be used to decrease joint swelling, tenderness, pain and stiffness in mammalian species, such as dogs and monkeys, e.g., in conditions such as rheumatoid arthritis.

Compounds of formula I or a physiologically acceptable acid-addition or base-addition salt thereof may be compounded for such uses according to accepted pharmaceutical practice in oral dosage forms such as tablets, capsules, elixirs or powders for administration of about 100 mg to 2 gm per day, preferably 100 mg to 1 gm per day in two to four divided doses.

The following Examples further illustrate and represent preferred embodiments of the invention. All temperatures are expressed in degrees Centigrade.

EXAMPLE 1

2'-[[[4-(3,6-Dihydro-4-phenyl-1(2H)-pyridinyl)butyl]amino]-carbonyl][1,1'-biphenyl]-2-carboxylic acid A. 3,6-Dihydro-4-phenyl-1(2H)-pyridinebutanenitrile, hydrochloride (1:1)

4-Phenyl-1,2,3,6-tetrahydropyridine is prepared from 25 g (128 mmol) of the hydrochloride salt (dissolved in chloroform, washed with 10% KOH, water, dried, and the solvent evaporated). The residue, 19.85 g (134 mM) of 4-bromobutyronitrile, and 10 g of sodium carbonate are refluxed in 200 ml of benzene overnight. The benzene reaction mixture is filtered from the sodium carbonate and the solvent removed in vacuo. The residue is taken up in hot methanol (130 ml), filtered hot, and hot water (100 ml) added until precipitation occurs. The crystals are filtered off from the cooled mixture, dissolved in dioxane and the salt precipitated with HCl/dioxane: to yield 28.6 g of the title compound.

B. 3,6-Dihydro-4-phenyl-1(2H)-pyridinebutanamine, hydrochloride (1:2)

20.6 g (78.4 mM) 3,6-Dihydro-4-phenyl-1(2H)-pyridine-butanenitrile is prepared from the hydrochloride salt obtained from part A dissolved in chloroform, washed with 10% KOH, water, dried and the solvent evaporated). The residue is dissolved in 500 ml of ether and filtered from a small amount of insoluble material. 4.47 g (117.7 mM) of Lithium aluminum hydride (1.5 eq) is added to the solution which is refluxed for 4 hours. The excess lithium aluminum hydride is destroyed by the sequential addition of 4.5 ml of water, 4.5 ml of 20% NaOH and 13.5 ml of water. The ether is filtered from the inorganic salts, washed with saturated NaCl solution, dried (Na$_2$SO$_4$), and the salt precipitated by addition of ethereal HCl. Conversion to the free base, neutralization of an alcohol solution with alcoholic HCl and precipitation by the addition of dioxane gives 13.45 g of the title compound, mp 241°–244° (dec).

C. 2'-[[[4-(3,6-Dihydro-4-phenyl-1(2H)-pyridinyl)butyl]amino]carbonyl][1,1'-biphenyl]-2-carboxylic acid The compound as prepared in part B (16.23 g, 53.5 mM) is converted to its free base, combined with diphenic anhydride (12.0 g, 53.5 mM) and refluxed in 500 ml of toluene for 2 hours. The product is allowed to crystallize out overnight at room temperature. The crystals are filtered off, washed with toluene, and dried at 80° under vacuum to yield 23.75 g of crude material m.p. 183°–192°.

Recrystallization of 4 g of the crude material from ethanol gives 3.63 g of the title compound, m.p. 196°–198° decomp.

EXAMPLE 2

2'-[[[3-(4-Phenyl-1-piperidinyl)propyl]amino]carbonyl][1,1'-biphenyl]-2-carboxylic acid A. 4-Phenyl-1-piperidinepropanamine, hydrochloride (1:2)

The above compound is prepared as described in Example 1A and B except that 4-phenylpiperidine is employed in place of 4-phenyl-1,2,3,6-tetrahydropyridine and chloropropionitrile is used in place of 4-bromobutyronitrile.

B. 2'-[[[3-(4-phenyl-1-piperidinyl)propyl]amino]carbonyl][1,1'-biphenyl]-2-carboxylic acid 4-Phenyl-1-piperidinepropanamine, hydrochloride (prepared in part A) (16.33 g, 53.5 mM) and diphenic anhydride (12.0 g, 53.5 mM) are refluxed in toluene for 2 hours. The mixture is allowed to stand overnight at room temperature during which time product crystallizes out. The crystals are filtered off, washed with toluene, recrystallized from ethanol, and dried at 80° to give the title compound.

EXAMPLES 3 TO 22

Following the procedure of Example 1, part A, except substituting the 4-phenylpyridine compound as indicated in column A of Table I set out below for 4-phenyl-1,2,3,6-tetrahydropyridine and substituting the halo alkyl nitrile as indicated in column B for 4-bromobutyronitrile, the following 3,6-dihydro-4-phenyl-1(2H)pyridinealkylamine starting materials are obtained as indicated in column C.

Table I

| Ex. No. | Column A X (position) | Column B HalZ'CN | Column C |
|---|---|---|---|
| 3. | $CH_3$ (4) | $Br(CH_2)_3CN$ | 3,6-dihydro-4-(4-methyl-phenyl)-1(2H)pyridine-butanamine, HCl |
| 4. | $CH_3O$ (4) | $BrCH_2CN$ | 3,6-dihydro-4-(4-methoxy-phenyl)-1(2H)pyridine-ethanamine, HCl |
| 5. | Cl (3) | $Cl(CH_2)_2CN$ | 3,6-dihydro-4-(3-chloro-phenyl)-1(2H)pyridine-propanamine, HCl |
| 6. | $C_4H_9$ (3) | $Br(CH_2)_3CN$ | 3,6-dihydro-4-(3-butyl-phenyl)-1(2H)pyridine-butanamine, HCl |
| 7. | $NH_2$ (2) | $Cl(CH_2)_4CN$ | 3,6-dihydro-4-(2-amino-phenyl)-1(2H)pyridine-pentanamine, HCl |
| 8. | $NO_2$ (2) | $Br(CH_2)_5CN$ | 3,6-dihydro-4-(2-nitro-phenyl)-1(2H)pyridine-hexanamine, HCl |
| 9. | Br (2) | $ClCH_2CN$ | 3,6-dihydro-4-(2-bromo-phenyl)-1(2H)pyridine-ethanamine, HCl |
| 10. | $C_2H_5O$ (2) | $Br(CH_2)_2CN$ | 3,6-dihydro-4-(2-ethoxyphenyl)-1(2H)pyridinepropanamine, HCl |
| 11. | $CF_3$ (2) | $Br(CH_2)_3CN$ | 3,6-dihydro-4-[2-(trifluoro-methyl)phenyl]-1(2H)-pyridine-butanamine, HCl |
| 12. | $C_3H_7$ (3) | $Br(CH_2)_4CN$ | 3,6-dihydro-4-(3-propylphenyl)-1(2H)-pyridinepentanamine, HCl |
| 13. | $C_4H_9O$ (3) | $Br(CH_2)_5CN$ | 3,6-dihydro-3-(3-butoxyphenyl)-1(2H)pyridinehexanamine, HCl |
| 14. | $NH_2$ (3) | $ClCH_2CN$ | 3,6-dihydro-4-(3-aminophenyl)-1(2H)pyridineethanamine, HCl |
| 15. | $NO_2$ (3) | $Cl(CH_2)_2CN$ | 3,6-dihydro-4-(3-nitrophenyl)-1(2H)pyridinepropanamine, HCl |
| 16. | F (4) | $Cl(CH_2)_3CN$ | 3,6-dihydro-4-(4-fluorophenyl)-1(2H)pyridinebutanamine, HCl |
| 17. | $NH_2$ (4) | $BrCH_2CHCN$ with $CH_3$ | 3,6-dihydro-4-(4-aminophenyl)-β-methyl-1(2H)pyridinepropanamine, HCl |
| 18. | $NO_2$ (4) | $Br(CH_2)_3CN$ | 3,6-dihydro-4-(4-nitrophenyl)-1(2H)pyridinebutanamine, HCl |
| 19. | $C_4H_9$ (4) | $Br(CH_2)_3CN$ | 3,6-dihydro-4-(4-butylphenyl)-1(2H)-pyridinebutanamine, HCl |
| 20. | H | $BrCHCCH_2CN$ with $CH_3$ / $CH_3$ | 3,6-dihydro-4-phenyl-γ,γ-dimethyl 1(2H)pyridinebutanamine, HCl |
| 21. | H | $BrCHCN$ with $CH_3$ | 3,6-dihydro-4-phenyl-β-methyl-1(2H)pyridineethanamine, HCl |
| 22. | I (4) | $Br(CH_2)_3CN$ | 3,6-dihydro-4-(4-iodophenyl)-1(2H)pyridinebutanamine, HCl |

EXAMPLES 23 to 46

Following the procedure of Example 2, part A, but substituting the 4-phenylpiperidine compound as indicated in column A of Table II below for 4-phenylpiperidine, and substituting the haloalkyl nitrile for 4-bromopropanonitrile as indicated in column B, the following 4-phenyl-1-piperidinealkylamine starting materials are obtained as indicated in column C.

Table II

| Ex. No. | Column A | | Column B | Column C |
|---|---|---|---|---|
| | X (position) | | HalZ'CN | |
| 23 | H | | $Br(CH_2)_3CN$ | 4-phenyl-1-piperidinebutanamine, HCl |
| 24 | H | | $BrCH_2CN$ | 4-phenyl-1-piperidineethanamine, HCl |
| 25 | H | | $Cl(CH_2)_2CN$ | 4-phenyl-1-piperidinepropanamine, HCl |
| 26 | H | | $Br(CH_2)_4CN$ | 4-phenyl-1-piperidinepentanamine, HCl |
| 27 | H | | $\quad CH_3$ <br> $\quad\ \|$ <br> $ClCH_2CHCH_2CN$ | 4-phenyl-γ-methyl-1-piperidinebutanamine, HCl |
| 28 | $CH_3$ (4) | | $BrCH_2CN$ | 4-(4-methylphenyl)-1-piperidineethanamine, HCl |
| 29 | $C_2H_5O$ (4) | | $Br(CH_2)_2CN$ | 4-(4-ethoxyphenyl)-1-piperidinepropanamine, HCl |
| 30 | $C_4H_9$ (4) | | $Br(CH_2)_3CN$ | 4-(4-butoxyphenyl)-1-piperidinebutanamine, HCl |
| 31 | $NO_2$ (4) | | $Cl(CH_2)_4CN$ | 4-(4-nitrophenyl)-1-piperidinepentanamine, HCl |
| 32 | $NH_2$ (4) | | $Br(CH_2)_5CN$ | 4-(4-aminophenyl)-1-piperidinehexanamine, HCl |
| 33 | Cl (4) | | $ClCH_2CN$ | 4-(4-chlorophenyl)-1-piperidineethanamine, HCl |
| 34 | Br (3) | | $Cl(CH_2)_2CN$ | 4-(3-bromophenyl)-1-piperidinepropanamine, HCl |
| 35 | $NH_2$ (3) | | $Br(CH_2)_3CN$ | 4-(3-aminophenyl)-1-piperidinebutanamine, HCl |
| 36 | $NO_2$ (3) | | $Cl(CH_2)_3CN$ | 4-(3-nitrophenyl)-1-piperidinebutanamine, HCl |
| 37 | $C_4H_9O$ (3) | | $Br(CH_2)_4CN$ | 4-(3-butoxyphenyl)-1-piperidinepentanamine |
| 38 | $C_3H_7O$ (3) | | $ClCH_2CN$ | 4-(3-propoxyphenyl)-1-piperidineethanamine, HCl |
| 39 | $C_4H_9$ (3) | | $Cl(CH_2)_3CN$ | 4-(3-butylphenyl)-1-piperidinebutanamine, HCl |
| 40 | $C_2H_5$ (2) | | $Cl(CH_2)_3CN$ | 4-(2-ethylphenyl)-1-piperidinebutanamine, HCl |
| 41 | $CH_3$ (2) | | $BrCH_2CN$ | 4-(2-methylphenyl)-1-piperidineethanamine, HCl |
| 42 | $C_4H_9O$ (2) | | $Cl(CH_2)_2CN$ | 4-(2-butoxyphenyl)-1-piperidinepropanamine, HCl |
| 43 | I (2) | | $Cl(CH_2)_3CN$ | 4-(2-iodophenyl)-1-piperidinebutanamine, HCl |
| 44 | $NH_2$ (2) | | $Cl(CH_2)_4CN$ | 4-(2-aminophenyl)-1-piperidinepentanamine, HCl |
| 45 | $CF_3$ (3) | | $Br(CH_2)_5CN$ | 4-[3-(trifluoromethyl)phenyl]-1-piperidinehexanamine, HCl |
| 46 | $NO_2$ (2) | | $ClCH_2CN$ | 4-(2-nitrophenyl)-1-piperidineethanamine, HCl |

EXAMPLE 47

Dibenz[c,e]oxapine-5,7-dione

References: CA 52 1964f (1957); CA 54 8058b (1959)

A mixture of diphenic acid (100 g, 0.413M), 200 ml acetic acid, and 200 ml acetic anhydride is refluxed under nitrogen for 30 minutes and allowed to stand for 5 hours. The resulting crystals are filtered off, washed with acetic anhydride, water, 5% $NaHCO_3$, dried over KOH (vacuum at 60° overnight) to give the title compound 75.76 g (82%) (mp 222°–223°).

EXAMPLES 48 to 66

Following the procedure of Example 47 but substituting the diphenic acid as indicated in column A of Table III set out below for diphenic acid, the substituted diphenic anhydride set out in column B is obtained.

Table III

| Ex. No. | Column A | Column B |
|---|---|---|

Table III-continued

| Ex. No. | Column A | | Column B |
|---|---|---|---|
| | Y (position) | Y' (position) | |
| 48. | $C_2H_5$ (4) | $C_2H_5$ (4') | 3,9-diethyl-dibenz[c,e]-oxepine-5,7-dione |
| 49. | $CH_3$ (5) | $CH_3$ (5') | 2,10-dimethyl-dibenz[c,e]-oxepine-5,7-dione |
| 50. | Cl (4) | Cl (4') | 3,9-dichloro-dibenz[c,e]-oxepine-5,7-dione |
| 51. | F (5) | F (5') | 2,10-difluoro-dibenz[c,e]-oxepine-5,7-dione |
| 52. | $CF_3$ (4) | $CF_3$ (4') | 3,9-di-(trifluoromethyl)-dibenz[c,e]-oxepine-5,7-dione |
| 53. | $CF_3$ (5) | $CF_3$ (5') | 2,10-di-(trifluoromethyl)-dibenz[c,e]-oxepine-5,7-dione |
| 54. | $CH_3O$ (4) | $CH_3O$ (4') | 3,9-dimethoxy-dibenz[c,e]-oxepine-5,7-dione |
| 55. | $C_2H_5O$ (5) | $C_2H_5O$ (5') | 2,10-diethoxy-dibenz[c,e]-oxepine-5,7-dione |
| 56. | $C_3H_7$ (5) | $C_3H_7$ (5') | 2,10-dipropyl-dibenz[c,e]-oxepine-5,7-dione |
| 57. | $NO_2$ (4) | $NO_2$ (4') | 3,9-dinitro-dibenz[c,e]-oxepine-5,7-dione |
| 58. | $NO_2$ (5) | $NO_2$ (5') | 2,10-dinitro-dibenz[c,e]oxepin-5,7-dione |
| 59. | $C_3H_7O$ (4) | $C_3H_7O$ (4') | 3,9-dipropoxy-dibenz[c,e]-oxepine-5,7-dione |
| 60. | $NH_2$ (4) | $NH_2$ (4') | 3,9-diamino-dibenz[c,e]-oxepine-5,7-dione |
| 61. | $NH_2$ (5) | $NH_2$ (5') | 2,10-diamino-dibenz[c,e]-oxepine-5,7-dione |
| 62. | $C_4H_9$ (4) | $C_4H_9$ (4') | 3,9-dibutyl-dibenz[c,e]-oxepine-5,7-dione |
| 63. | CH (4) | CN (4') | 3,9-dicyano-dibenz[c,e]-oxepine-5,7-dione |
| 64. | CN (5) | CN (5') | 2,10-dicyano-dibenz[c,e]-oxepine-5,7-dione |
| 65. | $C_4H_9O$ (4) | $C_4H_9O$ (4') | 3,9-dibutoxy-dibenz[c,e]-oxepine-5,7-dione |
| 66. | $C_4H_9O$ (5) | $C_4H_9O$ (5') | 2,10-dibutoxy-dibenz[c,e]-oxepine-5,7-dione |

EXAMPLES 67 to 86

Following the procedure of Example 1, but substituting the 3,6-dihydro-4-(phenyl or substituted phenyl)-1(2H)-pyridinealkylamine, as listed in column A of Table IV and prepared as described in Examples 3 to 22 for the 3,6-dihydro-4-phenyl-1(2H)-pyridinebutanamine, HCl, and substituting the diphenic anhydride as listed in column B and prepared as described in Examples 47 to 66 for diphenic anhydride, the products listed in column C are obtained.

Table IV

| Ex. No. | Column A | Column B | Column C |
|---|---|---|---|
| 67. | 3,6-dihydro-4-(4-methylphenyl)-1(2H)pyridinebutanamine, HCl | 3,9-dimethyl-dibenz[c,e]-oxepine-5,7-dione | 2'-[[[4-(3,6-dihydro-4-(4-methylphenyl)-1(2H)-pyridinyl)bityl]amino]carbonyl]-[1,1'-(4,4'-dimethyl)biphenyl]-2-carboxylic acid |
| 68. | 3,6-dihydro-4-(4-methoxyphenyl)-1(2H)pyridineethanamine, HCl | 3,9-diethyl-dibenz[c,e]-oxepine-5,7-dione | 2'-[[[2-(3,6-dihydro-4-(4-methoxyphenyl)-1(2H)-pyridinyl)ethyl]amino]carbonyl]-[1,1',(4,4'-diethyl)biphenyl]-2-carboxylic acid |
| 69. | 3,6-dihydro-4-(3-chlorophenyl)-1(2H)pyridinepropanamine, HCl | 2,10-dimethyl-dibenz[c,e]-oxepine-5,7-dione [1,1'-(5,5'-dimethyl)biphenyl]-2- | 2'-[[[3-(3,6-dihydro-4-(3-chlorophenyl)-1(2H)-pyridinyl)propyl]amino]carbonyl]-carboxylic acid |
| 70. | 3,6-dihydro-4-(2-butylphenyl)-1(2H)pyridinebutanamine, HCl | 3,9-dichloro-dibenz[c,e]-oxepine-5,7-dione | 2'-[[[4-(3,6-dihydro-4-(2-butylphenyl)-1(2H)-pyridinyl)butyl]amino]carbonyl]-[1,1'-(4,4-dichloro)biphenyl]-2-carboxylic acid |
| 71. | 3,6-dihydro-4-(2-aminophenyl)-1(2H)pyridinepentanamine, HCl | 2,10-difluoro-dibenz[c,e]-oxepine-5,7-dione | 2'-[[[5-(3,6-dihydro-4-(2-aminophenyl)-1(2H)-pyridinyl)]amino]carbonyl]-[1,1'-(5,5'-difluoro)biphenyl]-2-carboxylic acid |
| 72. | 3,6-dihydro-4-(2-nitrophenyl)-1(2H)pyridinehexanamine, HCl | 3,9-di(trifluoromethyl)dibenz-[c,e]-oxepine-5,7-dione | 2'-[[[6-(3,6-dihydro-4-(2-nitrophenyl)-1(2H)-pyridinyl)hexyl]amino]carbonyl]-[1,1'-(4,4'-di-(trifluoromethyl)biphenyl]-2-carboxylic acid |
| 73. | 3,6-dihydro-4-(2-bromophenyl)-1(2H)pyridineethanamine, HCl | 2,10-di-(trifluoromethyl)dibenz-[c,e]-oxepine-5,7-dione | 2'-[[[2-(3,6-dihydro-4-(2-bromophenyl)-1(2H)-pyridinyl)ethyl]amino]carbonyl]-[1,1'-(5,5'-di-(trifluoromethyl)biphenyl]-2-carboxylic acid |
| 74. | 3,6-dihydro-4-(2-ethoxyphenyl)-1(2H)pyridinepropanamine, HCl | 3,9-dimethoxy-dibenz[c,e]-oxepine-5,7-dione | 2'-[[[3-(3,6-dihydro-4-(2-ethoxyphenyl)-1(2H)-pyridinyl)propyl]amino]carbonyl]- |

Table IV-continued

| Ex. No. | Column A | Column B | Column C |
|---|---|---|---|
| 75. | 3,6-dihydro-4-[2-(trifluoromethyl)phenyl]-1(2H)pyridinebutanamine, HCl | 2,10-diethoxy-dibenz[c,e]-oxepine-5,7-dione | 2'-[[[4-[2-(trifluoromethyl)phenyl]-1(2H)-pyridinyl)butyl]amino]carbonyl]-[1,1'-(5,5-diethoxy)biphenyl]-2-carboxylic acid |
| 76. | 3,6-dihydro-4-(3-propylphenyl)-1(2H)pyridinepentanamine, HCl | 2,10-dipropyl-dibenz[c,e]-oxepine-5,7-dione | 2'-[[[5-(3,6-dihydro-4-(3-propylphenyl)-1(2H)-pyridinyl)pentyl]amino]carbonyl]-[1,1'-(5,5'-dipropyl)biphenyl]-2-carboxylic acid |
| 77. | 3,6-dihydro-4-(3-butoxyphenyl)-1(2H)pyridinehexanamine, HCl | 3,9-dinitro-dibenz[c,e]-oxepine-5,7-dione | 2'-[[[6-(3,6-dihyddro-4-(3-butoxyphenyl)-1(2H)-pyridinyl)hexyl]amino]carbonyl]-(1,1'-(4,4'-dinitro)biphenyl]-2-carboxylic acid |
| 78. | 3,6-dihydro-4-(3-aminophenyl)-1(2H)pyridineethanamine, HCl | 2,10-dinitro-dibenz[c,e]-oxepine-5,7-dione | 2'-[[[2-(3,6-dihydro-4-(3-aminophenyl)-1(2H)-pyridinyl)ethyl]amino]carbonyl]-[1,1'-(5,5'-dinitro)biphenyl]-2-carboxylic acid |
| 79. | 3,6-dihydro-4-(3-nitrophenyl)-1(2H)pyridinepropanamine, HCl | 3,9-dipropoxy-dibenz[c,e]-oxepine-5,7-dione | 2'-[[[3-(3,6-dihydro-4-(3-nitrophenyl)-1(2H)-pyridinyl)propyl]amino]carbonyl]-[1,1'-(4,4'-dipropoxy)biphenyl]-2-carboxylic acid |
| 80. | 3,6-dihydro-4-(4-fluorophenyl)-1(2H)pyridinebutanamine, HCl | 3,9-diamino-dibenz[c,e]-oxpeine-5,7-dione | 2'-[[[4-(3,6-dihydro-4-(4-fluorophenyl)-1(2H)-pyridinyl)butyl]amino]carbonyl]-[1,1'-(4,4'-diamino)biphenyl]-2-carboxylic acid |
| 81. | 3,6-dihydro-4-(4-aminophenyl)-β-methyl-1(2H)pyridinepropanamine, HCl | 2,10-diamino-dibenz[c,e]-oxepine,5,7-dione | 2'-[[[3-(3,6-dihydro-4-(4-aminophenyl)-1(2H)-pyridinyl)-2-methylpropyl]amino]-carbonyl][1,1'-(5,5'-diamino)biphenyl]-2-carboxylic acid |
| 82. | 3,6-dihydro-4-(4-nitrophenyl)-1(2H)pyridinebutanamine, HCl | 3,9-dibutyl-dibenz[c,e]-oxepine-5,7-dione | 2'-[[[4-(3,6-dihydro-4-(4-nitrophenyl)-1(2H)-pyridinyl)butyl]amino]carbonyl]-[1,1'-(4,4'-dibutyl)biphenyl]-2-carboxylic acid |
| 83. | 3,6-dihydro-4-(4-butylphenyl)-1(2H)pyridinebutanamine, HCl | 3,9 dicyano-dibenz[c,e]-oxepine-5,7-dione | 2'-[[[4-(3,6-dihydro-4-(4-butylphenyl)-1(2H)-pyridinyl)butyl]amino]carbonyl]-[1,1'-(4,4'-dicyano)biphenyl]-2-carboxylic acid |
| 84. | 3,6-dihydro-4-phenyl-γ,γ-dimethyl-1(2H)pyridinebutanamine, HCl | 2,10-dicyano-dibenz[c,e]-oxepine-5,7-dione | 2'-[[[4-(3,6-dihydro-4-phenyl-1-(2H)-pyridinyl)-3,3-dimethylbutyl]amino]-carbonyl][1,1'-(5,5'-dicyano)biphenyl]-2-carboxylic acid |
| 85. | 3,6-dihydro-4-phenyl-β-methyl-1(2H)pyridineethanamine, HCl | 3,9-dibutoxy-dibenz[c,e]-oxepine-5,7-dione | 2'-[[[2-(3,6-dihydro-4-phenyl-1(2H)-pyridinyl)-2-methylethyl[amino]carbonyl]-[1,1'-(4,4'-dibutoxy)biphenyl]-2-carboxylic acid |
| 86. | 3,6-dihydro-4-(4-butylphenyl)-1(2H)pyridinebutanamine, HCl | 2,10-dibutoxy-dibenz[c,e]-oxepine-5,7-dione | 2'-[[[4-(3,6-dihydro-4-(4-butylphenyl)-1(2H)-pyridinyl)butyl]amino]carbonyl]-[1,1'-(5,5'-dibutoxy)biphenyl]-2-carboxylic acid |

EXAMPLES 87 to 110

Following the procedure of Example 2, but substituting the 4-(phenyl or substituted phenyl)piperidine alkylamine as listed in Column A of Table V and prepared as described in Examples 2 and 23 to 46 for the 4-phenylpiperidinepropylamine, HCl, and substituting the diphenic anhydride as listed in column B and prepared as described in Examples 47 to 66 for diphenic anhydride, the products listed in column C are obtained.

Table V

| Ex. No. | Column A | Column B | Column C |
|---|---|---|---|
| 87 | 4-phenyl-1-piperidinebutanamine, HCl | 3,9-dimethyl-dibenz[c,e]-oxepine-5,7-dione | 2'-[[[4-(4-phenyl-1-piperidinyl)butyl]-amino]carbonyl][1,1'-(4,4'-dimethyl)-biphenyl]-2-carboxylic acid |
| 88. | 4-phenyl-1-piperidineethanamine, HCl | 3,9-diethyl-dibenz[c,e]-oxepine-5,7-dione | 2'-[[[2-(4-phenyl-1-piperidinyl)ethyl]-amino]carbonyl][1,1'-(4,4'-diethyl)-biphenyl]-2-carboxylic acid |
| 89. | 4-phenyl-1-piperidinepropanamine, HCl | 2,10-dimethyl-dibenz[c,e]-oxepine-5,7-dione | 2'-[[[3-(4-phenyl-1-piperidinyl)propyl]-amino]carbonyl][1,1'-(5,5'-dimethyl)-biphenyl]-2-carboxylic acid |
| 90. | 4-phenyl-1-piperidinebutanamine, HCl | 3,9-dichloro-dibenz;(c,e]-oxepine-5,7-dione | 2'-[[[4-(4-phenyl-1-piperidinyl)butyl]-amino]carbonyl][1,1'-(4,4'-dichloro)-biphenyl]-2-carboxylic acid |
| 91. | 4-phenyl-γ-methyl-1-piperidine-butanamine, HCl | 2,10-difluoro-dibenz[c,e]-oxepine-5,7-dione | 2'-[[[4-(4-phenyl-1-piperidinyl)-3-methylbutyl]amino]cabonyl][1,1'-(5,5'-difluoro)biphenyl]-2-carboxylic acid |
| 92. | 4-(4-methylphenyl)-1-piperidine-ethanamine, HCl | 3,9-di-(trifluoromethyl)-dibenz-[c,e]-oxepine-5,6-dione | 2'-[[[2-[4-(4-methylphenyl)-1-piperidinyl]-ethyl]amino]carbonyl]['1,1'-[4,4'-di-(trifluoromethyl)bihpeyl]-2-carboxylic acid |
| 93. | 4-(4-ethoxyphenyl)-1-piperidine-propanamine, HCl | 2,10-di-(trifluoromethyl)-dibenz-[c,e]-oxepine-5,7-dione | 2'-[[[3-[4-(4-ethoxyphenyl)-1-piperidinyl]-propyl]amino]carboyl](1,1'-[5,5'-di-(trifluoromethyl[-2-carboxylic |

Table V-continued

| Ex. No. | Column A | Column B | Column C |
|---|---|---|---|
| 94. | 4-(4-butoxyphenyl)-1-piperidine-butanamine, HCl | 3,9-dimethoxy-dibenz[c,e]-oxepine-5,7-dione | 2'-[[[4-[4-(4-butoxyphenyl)-1-piperidinyl]-butyl]amino]carboyl][1,1'-(4,4'-dimethoxy)-biphenyl]-2-carboxylic acid |
| 95. | 4-(4-nitrophenyl)-1-piperidino-pentanamine, HCl | 2,10-diethoxy-dibenz[c,e]-oxepine-5,7-dione | 2'-[[[5-[4-(4-nitrophenyl)-1-piperidinyl]-pentyl]amino]carboyl][1,1'-5,5'-diethoxy)biphenyl]-2-carboxylic acid |
| 96. | 4-(4-aminophenyl)-1-piperidine-hexanamine, HCl | 2,10-dipropyl-bibenz[c,e]-oxepine-5,7-dione | 2'-[[[6-[4-(4-aminophenyl)-1-piperidinyl]-hexyl]amino]carbonyl][1,1'-(5,5'-dipropyl)biphenyl]-2-carboxylic acid |
| 97. | 4-(4-chlorophenyl)-1-piperidine-ethanamine, HCl | 3,9-dinitro-dibenz[c,e]-oxepine-5,7-dione | 2'-[[[2-[4-(4-chlorophenyl)-1-piperidinyl]-ethyl]amino]carbonyl][1,1'-(4,4'-dinitro)biphenyl]-2-carboxylic acid |
| 98. | 4-(3-bromophenyl)-1-piperidine-propanamine, HCl | 2,10-dinitro-dibenz[c,e]-oxepine-5,7-dione | 2'-[[[3-[4-(3-bromophenyl)-1-piperidinyl]-propyl]amino]carbonyl][1,1'-(5,5'-dinitro)biphenyl]-2-carboxylic acid |
| 99. | 4-(3-aminophenyl)-1-piperidine-3,9-dipropoxy-dibenz[c,e]-butanamine, HCl | 2'-[[[4-[4-(3-aminophenyl)-1-piperidinyl]-oxepine-5,7-dione | butyl]amino]carbonyl][1,1'-(4,4'-dipropoxy)biphenyl]-2-carboxylic acid |
| 100. | 4-(3-nitrophenyl)-1-piperidine-butanamine, HCl | 3,9-diamino-dibenz[c,e]-oxepine-5,7-dione | 2'-[[[4-[4-(3-nitrophenyl)-1-piperidinyl]-butyl]amino]carbonyl][1,1'-(4,4'-diamino)biphenyl]-2-carboxylic acid |
| 101. | 4-(3-butoxyphenyl)-1-piperidine-pentanamine, HCl | 2,10-diamino-dibenz[c,e]-oxepine-5,7-dione | 2'-[[[5-[4-(3-butoxyphenyl)-1-piperidinyl]-pentyl]amino]carbonyl][1,1'-(5,5'-diamino)biphenyl]-2-carboxylic acid |
| 102. | 4-(3-propoxyphenyl)-1-piperidine-ethanamine, HCl | 3,9-dibutyl-dibenz[c,e]-oxepine-5,7-dione | 2'-[[[2-[4-(4-propoxyphenyl)-1-piperidinyl]-ethyl]amino]carboyl][1,1'-(4,4'-dibutyl)biphenyl]-2-carboxylic acid |
| 103. | 4-(3-t-butylphenyl)-1-piperidine-butanamine, HCl | 3,9-dicyano-dibenz[c,e]-oxepine-5,7-dione | 2'-[[[4-[4-(3-t-butylphenyl)-1-piperidinyl]-butyl]amino]carbonyl][1,1'-(4,4'-dicyano)biphenyl]-2-carboxylic acid |
| 104. | 4-(2-ethylphenyl)-1-piperidine-butanamine, HCl | 2,10-dicyano-dibenz[c,e]-oxepine-5,7-dione | 2'-[[[4-( 4-(2-ethylphenyl)-1-piperidinyl]-butyl]amino]carbonyl][1,1'-(5,5'-dicyano)biphenyl]-2-carboxylic acid |
| 105. | 4-(2-methylphenyl)-1-piperidine-ethanamine, HCl | 3,9-dibutoxy-dibenz[c,e]-oxepine-5,7-dione | 2'-[[[2-[4-(2-methylphenyl)-1-piperidinyl]-ethyl]amino]carbonyl][1,1'-(4,4'-dibutoxy)biphenyl]-2-carboxylic acid |
| 106. | 4-(2-butoxyphenyl)-1-piperidine-propanamine, HCl | 2,10-dibutoxy-dibenz[c,e]-oxepine-5,7-dione | 2'-[[[3-[4-(2-butoxyphenyl)-1-piperidinyl]-propyl]amino]carbonyl][1,1'-(5,5'-dibutoxy)biphenyl]-2-carboxylic acid |
| 107. | 4-(2-iodophenyl)-1-piperidine-butanamine, HCl | 3,9-dimethyl-dibenz[c,e]-oxepine-5,7-dione | 2'-[[[4-[4-(2-iodophenyl)-1-piperidinyl]-butyl]amino]carboyl][1,1'-(4,4'-dimethyl)biphenyl]-2-carboxylic acid |
| 108. | 4-(2-aminophenyl)-1-piperidine-/3,9-dipropyl-dibenZ[c,e]-pentanamine, HCl | 2'-[[[5-[4-(2-aminophenyl)-1-piperidinyl]-oxepine-5,7-dione oxepine-5,7-dione | pentyl]amino]carbonyl]( 1,1'-(4,4'-dipropyl)biphenyl]-2-carboxylic acid |
| 109. | 4-[3-(trifluoromethyl)phenyl]-1-piperidinehexanamine, HCl | 2,10-diethyl-dibenz[c,e]-oxepine-5,7-dione | 2'-[[[6-[4-[3-(trifluoromethyl)phenyl]-piperidinyl]hexyl]amino]carbonyl]-[1,1'-(5,5'-diethyl)biphenyl]-2-carboxylic acid |
| 110. | 4-(2-nitrophenyl)-1-piperidine-ethanamine, HCl | 3,9-dimethyl-dibenz[c,e]-oxepine-5,7-dione | 2'-[[[2-[4-(2-nitrophenyl)-1-piperidinyl]-ethyl]amino]carbonyl][1,1'-(4,4'-dimethyl)biphenyl]-2-carboxylic acid |

What is claimed is:

1. A compound having the formula

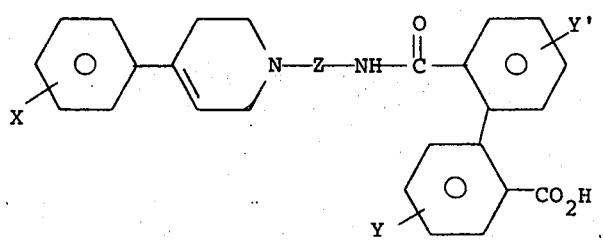

wherein X is a member selected from the group consisting of hydrogen, lower alkyl, lower alkoxy, halogen, amino, trifluoromethyl, and nitro; Y and Y' are the same and are members selected from the group consisting of hydrogen, halogen, trifluoromethyl, lower alkyl, lower alkoxy, nitro, amino, and cyano, and Y is at the 4- or 5-position and Y' is at the 4'- or 5'-position, provided when Y is at the 4-position, Y' is at the 4'-position and when Y is at the 5-position, Y' is at the 5'-position; Z is a straight or branched chain alkylene group containing from 2 to about 6 carbons; and pharmaceutically acceptable acid- or base-addition salts thereof.

2. A compound as defined in claim 1 wherein X is selected from the group consisting of hydrogen, lower alkoxy or halogen, and Y and Y' are selected from the group consisting of hydrogen, lower alkoxy or halogen.

3. A compound as defined in claim 1 wherein X, Y and Y' are hydrogen.

4. A compound as defined in claim 1 wherein Z contains 2 to 4 carbons.

5. A compound as defined in claim 1 having the name 2'-[[[4-(3,6-dihydro-4-phenyl-1(2H)-pyridinyl)butyl]-amino]carbonyl][1,1'-biphenyl]-2-carboxylic acid.

6. A pharmaceutical composition for use in treating inflammation comprising a compound as defined in claim 1 and an inert pharmaceutically acceptable carrier therefor.

7. A method of treating inflammation in mammalian species, which comprises orally administering to the mammalian host a therapeutic amount of a composition as defined in claim 6.

* * * * *

UNITED STATES PATENT AND TRADEMARK OFFICE
CERTIFICATE OF CORRECTION

PATENT NO. : 3,995,045
DATED : November 30, 1976
INVENTOR(S) : Peter C. Wade et al It is certified that error appears in the above-identified patent and that said Letters Patent are hereby corrected as shown below:

Column 9, Table III, Example 63, Column A, Y-position should read --CN(4)--.

Table IV, Example 67, Column C, line 2, "bityl" should read --butyl--.

Table IV, Example 68, Column C, line 3, "[1,1'," should read --[1,1'- --.

Table IV, Example 69, Column B should read --2,10-dimethyl-dibenz[c,e]-oxepine-5,7-dione-- and Column C should read --2'-[[[3-(3,6-dihydro-4-(3-chlorophenyl)-1(2H)-pyridinyl)-propyl]amino]carbonyl][1,1'-(5,5'-dimethyl)biphenyl]-2-carboxylic acid--.

Table IV, Example 71, Column C, line 2 should read --1(2H)-pyridinyl)pentyl]amino]carbonyl]- --.

Table IV, Example 72, Column B, first line, after "3,9-di" insert a hyphen.

Table IV, Example 75, Column C, line 3, "5,5" should read --5,5'--.

Table IV, Example 77, Column C, line 1, "dihyddro" should read --dihydro--.

Table IV, Example 80, Column B, line 2, "oxpeine" should read --oxepine--.

Table IV, Example 85, Column C, line 2 should read --pyridinyl)-2-methylethyl]amino]carbonyl]- --.

Table V, Example 90, Column B, line 1 should read --3,9-dichloro-dibenz[c,e]- --.

Table V, Example 93, Column C should read --2'-[[[3-[4-(4-ethoxyphenyl)-1-piperidinyl]propyl]amino]carbonyl]-[1,1'-[5,5'-di-(trifluoromethyl)biphenyl]-2-carboxylic acid--.

Table V, Example 94, Column C, line 2, "carboyl" should read --carbonyl--.

Table V, Example 95, Column A, line 1, "piperidino" should read --piperidine--.

UNITED STATES PATENT AND TRADEMARK OFFICE
CERTIFICATE OF CORRECTION

PATENT NO. : 3,995,045
DATED : November 30, 1976
INVENTOR(S) : Peter C. Wade et al It is certified that error appears in the above-identified patent and that said Letters Patent are hereby corrected as shown below:

Table V, Example 99, Column A should read --4-(3-amino-phenyl)-1-piperidine-butanamine, HCl--; Column B should read --3,9-dipropoxy-dibenz[c,e]-oxepine-5,7-dione-- and Column C should read --2'-[[[4-[4-(3-aminophenyl)-1-piperidinyl]butyl]amino]carbonyl][1,1'-(4,4'-dipropoxy)-biphenyl]-2-carboxylic acid--.

Table V, Example 101, Column C, line 2, "carboyl" should read --carbonyl--.

Table V, Example 102, Column C should read --2'-[[[2-[4-(3-propoxyphenyl)-1-piperidinyl]ethyl]amino]carbonyl]-[1,1'-(4,4'-dibutyl)biphenyl]-2-carboxylic acid--.

Table V, Example 104, Column C, line 1 should read --2'-[[[4-[4-(2-ethylphenyl)-1-piperidinyl]- --.

Table V, Example 107, Column C, line 2, "carboyl" should read --carbonyl--.

Table V, Example 108, Column A should read --4-(2-amino-phenyl)-1-piperidine-pentanamine, HCl--; Column B should read --3,9-dipropyl-dibenz[c,e]-oxepine-5,7-dione-- and Column C should read --2'-[[[5-[4-(2-aminophenyl)-1-piperidinyl]pentyl]amino]carbonyl][1,1'-(4,4'-dipropyl)-biphenyl]-2-carboxylic acid.--

Signed and Sealed this

Fifth Day of April 1977

[SEAL]

Attest:

RUTH C. MASON
Attesting Officer

C. MARSHALL DANN
Commissioner of Patents and Trademarks